United States Patent
Riedel et al.

[11] Patent Number: 6,020,444
[45] Date of Patent: *Feb. 1, 2000

[54] PROCESS FOR PREPARING A CYCLOOLEFIN COPOLYMER

[75] Inventors: Michael Riedel, Essen; Thomas Weller, Mainz; Alexandra Jacobs, Frankfurt, all of Germany

[73] Assignees: Hoechst AG, Frankfurt am Main, Germany; Mitsui Petrochemical Ind., Ltd., Tokyo, Japan

[ * ] Notice: This patent is subject to a terminal disclaimer.

[21] Appl. No.: 09/090,855

[22] Filed: Jun. 4, 1998

Related U.S. Application Data

[63] Continuation of application No. 08/766,622, Dec. 13, 1996, Pat. No. 5,869,586.

[30] Foreign Application Priority Data

Dec. 13, 1995 [DE] Germany ............... 195 46 500

[51] Int. Cl.[7] .................................. C08F 232/00
[52] U.S. Cl. .................. 526/170; 526/126; 526/127; 526/160; 526/161; 526/281; 526/308; 526/943
[58] Field of Search ........................ 526/160, 170, 526/281, 161, 943, 126, 127, 308

[56] References Cited

U.S. PATENT DOCUMENTS

| | | |
|---|---|---|
| 5,003,019 | 3/1991 | Ishimaru et al. . |
| 5,008,356 | 4/1991 | Ishimaru et al. ............ 526/281 |
| 5,087,677 | 2/1992 | Brekner et al. . |
| 5,324,800 | 6/1994 | Welborn, Jr. et al. . |
| 5,371,158 | 12/1994 | Brekner et al. ............ 526/281 X |
| 5,529,966 | 6/1996 | Luciani et al. . |
| 5,602,219 | 2/1997 | Aulbach et al. ............ 526/160 |

FOREIGN PATENT DOCUMENTS

| | | |
|---|---|---|
| 0 283 164 | 9/1988 | European Pat. Off. . |
| 0 129 368 | 7/1989 | European Pat. Off. . |
| 0 407 870 | 1/1991 | European Pat. Off. . |
| 0 595 390 | 5/1994 | European Pat. Off. . |
| 0 659 758 A1 | 6/1995 | European Pat. Off. . |
| WO 95/32979 | 12/1995 | WIPO . |

OTHER PUBLICATIONS

G. Chandra et al, "Amido–Derivatives of Metals and Metalloids", J. Chem. Soc. (A), 1968, pp. 1940–1945.

G. Chandra et al, Amido–Derivatives of Metals and Metalloids, J. Chem. Soc. (Q), 1968, pp. 1940–2001.

Ronald Halterman, "Synthesis and Applications of Chiral Cyclopentadienylmetal Complexes", Chem. Rev., 1992, 92, pp. 965–994.

*Primary Examiner*—Fred Teskin
*Attorney, Agent, or Firm*—Connolly Bove Lodge & Hutz LLP

[57] ABSTRACT

The present invention relates to a process for preparing a cycloolefin copolymer by polymerization of at least one cyclic olefin and at least one acyclic olefin in the presence of a catalyst comprising at least one metallocene compound of the formula I,

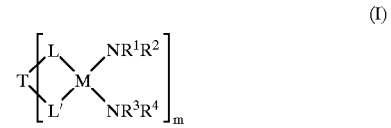

(I)

where L is a π-ligand, L' is a π-ligand, T is a bridge between L and L', M is a tetravalent transition metal, m is 1 or 2 and $R^1$, $R^2$, $R^3$ and $R^4$ are, independently of one another, identical or different and are each a hydrogen atom or a $C_1$–$C_{20}$-hydrocarbon radical.

10 Claims, No Drawings

PROCESS FOR PREPARING A CYCLOOLEFIN COPOLYMER

This application is a continuation of our application Ser. No. 08/766,622, filed Dec. 13, 1996, now U.S. Pat. No. 5,869,586, issued Feb. 9, 1999.

The present invention relates to a process for preparing a cycloolefin copolymer in the presence of a metallocene compound.

Metallocene compounds of the 4th transition group of the Periodic Table of the Elements are, in combination with methylaluminoxane (MAO), active catalysts for the polymerization of olefins. The literature discloses the preparation of polyolefins using soluble metallocene compounds in combination with aluminoxanes or other cocatalysts which, owing to their Lewis acidity, can convert the neutral metallocene into a cation and stabilize it (EP-A-129 368).

Metallocene and semisandwich complexes are of great interest not only in respect of the polymerization or oligomerization of olefins. They can also be used as hydrogenation, epoxidation, isomerization and C—C coupling catalysts (Chem. Rev. 1992, 92, 965–994).

It is known from the literature that CpH can be reacted with zirconium or hafnium dimethyltetraamide, directly and without addition of a base, to give metallocenes of the type described in EP-A-595 390 and EP-A-283 164 (J. Chem. Soc. (A), 1968, 1940–1945). Furthermore, it is known that cycloolefin copolymers can be prepared in the presence of bridged metallocenes (EP-A-283 164, EP-A-407 870). It is an object of the invention to provide an economical process for preparing cycloolefin copolymers. This object is achieved by the present invention.

The present invention accordingly provides a process for preparing a cycloolefin copolymer by polymerization of at least one cyclic olefin and at least one acyclic olefin in the presence of a catalyst comprising at least one metallocene compound of the formula I,

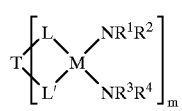

(I)

where L is a π-ligand, L' is a π-ligand, T is a bridge between L and L', M is a tetravalent transition metal, m is 1 or 2 and $R^1$, $R^2$, $R^3$ and $R^4$ are, independently of one another, identical or different and are each a hydrogen atom or a $C_1$–$C_{20}$-hydrocarbon radical.

M is preferably titanium, zirconium, hafnium, vanadium, niobium, tantalum, scandium, yttrium or a rare earth metal, particularly preferably titanium, zirconium or hafnium. L is preferably a substituted or unsubstituted cyclopentadienyl group. L' is preferably a substituted or unsubstituted cyclopentadienyl group. When m=1, T is preferably $[R^5R^6X]_n$, where X are, independently of one another, identical or different and are carbon, silicon, germanium or tin, the radicals $R^5$ and $R^6$ are, independently of one another, identical or different and are each a hydrogen atom or a $C_1$–$C_{30}$-hydrocarbon radical such as $C_1$–$C_{20}$-alkyl or $C_6$–$C_{20}$-aryl and n is 1, 2, 3 or 4, preferably 1 or 2. When m=2, T is preferably carbon, silicon, germanium or tin.

$R^1$ and $R^3$ are, independently of one another, identical or different and are each a hydrogen atom or a $C_1$–$C_{20}$-hydrocarbon radical, preferably a $C_1$–$C_{20}$-hydrocarbon radical such as $C_1$–$C_{20}$-alkyl or $C_6$–$C_{14}$-aryl, in particular methyl.

$R^2$ and $R^4$ are, independently of one another, identical or different and are preferably each a $C_1$–$C_{20}$-hydrocarbon radical such as $C_1$–$C_{20}$-alkyl or $C_6$–$C_{14}$-aryl, in particular methyl.

The radicals $R^1$, $R^2$, $R^3$ and $R^4$ are, independently of one another, identical or different. Preferably, the radicals $R^1$, $R^2$, $R^3$ and $R^4$ are identical and are $C_1$–$C_{20}$-alkyl or $C_6$–$C_{14}$-aryl, in particular methyl.

Examples of substituted cyclopentadienyl groups L or L' are:
tetramethylcyclopentadienyl, methylcyclopentadienyl, methyl-tert-butylcyclopentadienyl, tert-butylcyclopentadienyl,
isopropylcyclopentadienyl, dimethylcyclopentadienyl, trimethycyclopentadienyl,
trimethylethylcyclopentadienyl, phenylcyclopentadienyl, diphenylcyclopentadienyl,
indenyl, 2-methylindenyl, 2-ethylindenyl, 3-methylindenyl, 3-tert-butylindenyl,
3-trimethylsilylindenyl, 2-methyl-4-phenylindenyl, 2-ethyl-4-phenylindenyl,
2-methyl-4-naphthylindenyl, 2-methyl-4-isopropylindenyl, 4,5-benzoindenyl,
2-methyl-4,5-benzoindenyl, 2-methyl-α-acenaphthindenyl,
2-methyl-4,6-diisopropylindenyl, fluorenyl, 4-methylfluorenyl or
2,7-di-tert-butylfluorenyl.

Examples of bridges T are:
dimethylsilanediyl, methylphenylsilanediyl, diphenylsilanediyl, dimethylgermanediyl,
1,2-tetramethyldisilanediyl, 1,2-ethylidene, 1,2-propylidene, 1,2-butylidene,
1,3-propylidene, 1,4-butylidene or 2,2-propylidene.

Examples of metallocene compounds of the formula I are:
bis(dimethylamido)[η⁵:η⁵-2,2-(cyclopentadienyl)(indenyl) propylidene)]-zirconium
bis(dimethylamido)[η⁵:η⁵-2,2-(cyclopentadienyl)(indenyl) propylidene)]-hafnium
bis(dimethylamido)[η⁵:η⁵-2,2-(cyclopentadienyl) (fluorenyl)propylidene)]-zirconium
bis(dimethylamido)[η⁵:η⁵-2,2-(cyclopentadienyl) (fluorenyl)propylidene)]-hafnium
bis(dimethylamido)[η⁵:η⁵-2,2-(fluorenyl)(indenyl) propylidene)]zirconium
bis(dimethylamido)[η⁵:η⁵-2,2-(fluorenyl)(indenyl) propylidene)]hafnium
bis(dimethylamido)[η⁵:η⁵-2,2-(methylcyclopentadienyl) (indenyl)propylidene)]zirconium
bis(dimethylamido)[η⁵:η⁵-2,2-(methylcyclopentadienyl) (fluorenyl)propylidene)]-zirconium
bis(dimethylamido)[η⁵:η⁵-2,2-(fluorenyl)(2-methylindenyl)propylidene)]-zirconium
bis(dimethylamido)[η⁵:η⁵-2,2-(tetramethylcyclopentadienyl)(indenyl)-propylidene)] zirconium
bis(dimethylamido)[η⁵:η⁵-2,2-(tetramethylcyclopentadienyl)(fluorenyl)-propylidene)] zirconium
bis(dimethylamido)[η⁵:η⁵-2,2-(fluorenyl)(2-ethylindenyl) propylidene)]-zirconium
bis(dimethylamido)[η⁵:η⁵-2,2-(cyclopentadienyl)(2-methylindenyl)-propylidene)]zirconium
bis(dimethylamido)[η⁵:η⁵-2,2-(cyclopentadienyl)(2-ethylindenyl)-propylidene)]zirconium
bis(dimethylamido)[η⁵:η⁵-2,2-(cyclopentadienyl)(3-trimethylsilylindenyl)-propylidene)]zirconium
bis(dimethylamido)[η⁵:η⁵-2,2-(methylcyclopentadienyl)(2-methylindenyl)-propylidene)]zirconium bis(dimethylamido)[η$^5$:η$^5$-2,2-(methylcyclopentadienyl)(2-ethylindenyl)-propylidene)]zirconium
bis(dimethylamido)[η$^5$:η$^5$-2,2-(methylcyclopentadienyl)(3-trimethylsilylindenyl)propylidene)]zirconium
bis(dimethylamido)[dimethylsilanediyl(η$^5$:η$^5$-(cyclopentadienyl)(indenyl)]-zirconium
bis(dimethylamido)[dimethylsilanediyl(η$^5$:η$^5$-(cyclopentadienyl)(indenyl)]-zirconium
bis(dimethylamido)[dimethylsilanediyl(η$^5$:η$^5$-(fluorenyl)(indenyl)]zirconium
bis(dimethylamido)[dimethylsilanediyl(η$^5$:η$^5$-2,2-(methylcyclopentadienyl)-(indenyl))]zirconium
bis(dimethylamido)[dimethylsilanediyl(η$^5$:η$^5$-2,2-(methylcyclopentadienyl)-(fluorenyl))]zirconium
bis(dimethylamido)[dimethylsilanediyl(η$^5$:η$^5$-2,2-(fluorenyl)(2-methyl-indenyl))]zirconium
bis(dimethylamido)[dimethylsilanediyl(η$^5$:η$^5$-2,2-(tetramethylcyclopentadienyl)(indenyl))]zirconium
bis(dimethylamido)[dimethylsilanediyl(η$^5$:η$^5$-2,2-(tetramethylcyclopentadienyl)(fluorenyl))]zirconium
bis(dimethylamido)[dimethylsilanediyl(η$^5$:η$^5$-2,2-(fluorenyl)(2-ethylindenyl))]-zirconium
bis(dimethylamido)[dimethylsilanediyl(η$^5$:η$^5$-2,2-(cyclopentadienyl)(2-methylindenyl))]zirconium
bis(dimethylamido)[dimethylsilanediyl(η$^5$:η$^5$-2,2-(cyclopentadienyl)(2-ethyl-indenyl))]zirconium
bis(dimethylamido)[dimethylsilanediyl(η$^5$:η$^5$-2,2-(cyclopentadienyl)(3-trimethylsilylindenyl))]zirconium
bis(dimethylamido)[dimethylsilanediyl(η$^5$:η$^5$-2,2-(methylcyclopentadienyl)-(2-methylindenyl))]zirconium
bis(dimethylamido)[dimethylsilanediyl(η$^5$:η$^5$-2,2-(methylcyclopentadienyl)-(2-ethylindenyl))]zirconium
bis(dimethylamido)[dimethylsilanediyl(η$^5$:η$^5$-2,2-(methylcyclopentadienyl)-(3-trimethylsilylindenyl))]zirconium
stanntetraylbis[(η$^5$:η$^5$-bis(cyclopentadienyl)bis(dimethylamido)zirconium].

The preferred form of metallocene compound of the formula (I) used in the process of the invention is a metallocene compound of the formula (II)

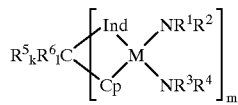

(II)

where Cp is an unsubstituted or substituted cyclopentadienyl group, Ind is unsubstituted or substituted indenyl, M is a tetravalent transition metal, R$^1$, R$^2$, R$^3$ and R$^4$ are, independently of one another, identical or different and are each a hydrogen atom or a C$_1$–C$_{20}$-hydrocarbon radical, R$^5$ and R$^6$ are, independently of one another, identical or different and are each a hydrogen atom or a C$_1$–C$_{30}$-hydrocarbon radical, m is 1 or 2 and k and l are 1 when m is 1 and k and l are zero when m is 2.

In formula II, M is preferably titanium, zirconium, hafnium, vanadium, niobium, tantalam, scandium, yttrium or a rare earth metal, particularly preferably titanium, zirconium or hafnium.

Cp is an unsubstituted or substituted cyclopentadienyl group.

Examples of substituted cyclopentadienyl groups Cp are:
tetramethylcyclopentadienyl, methylcyclopentadienyl, methyl-tert-butylcyclopentadienyl, tert-butylcyclopentadienyl, isopropylcyclopentadienyl, dimethylcyclopentadienyl, trimethylcyclopentadienyl, trimethylethylcyclopentadienyl, phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-Methyl-4-phenylindenyl, 2-ethyl-4-phenylindenyl, 2-methyl-4-naphthylindenyl, 2-methyl-4-isopropylindenyl, 4,5-benzoindenyl, 2-methyl-4,5-benzoindenyl, 2-methyl-α-acenaphthindenyl, 2-methyl-4,6-diisopropylindenyl, fluorenyl, 4-methylfluorenyl or 2,7-di-tert-butylfluorenyl.

Ind is unsubstituted or substituted indenyl. Examples of substituted indenyl are:
2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthylindenyl, 2-methyl-4-isopropylindenyl, 4,5-benzoindenyl, 2-methyl-4,5-benzoindenyl, 2-methyl-α-acenaphthindenyl, 2-methyl-4,6-diisopropylindenyl. Ind is preferably unsubstituted indenyl.

The radicals R$^5$ and R$^6$ are, independently of one another, identical or different, preferably identical, and are each a hydrogen atom or a C$_1$–C$_{30}$-hydrocarbon radical such as C$_1$–C$_{20}$-alkyl or C$_6$–C$_{20}$-aryl. Preferably, R$^5$ and R$^6$ are methyl or phenyl, in particular methyl.

R$^1$ and R$^3$ are, independently of one another, identical or different and are each a hydrogen atom or a C$_1$–C$_{20}$-hydrocarbon radical, preferably a C$_1$–C$_{20}$-hydrocarbon radical such as C$_1$–C$_{20}$-alkyl or C$_6$–C$_{14}$-aryl, in particular methyl.

R$^2$ and R$^4$ are, independently of one another, identical or different and are preferably a C$_1$–C$_{20}$-hydrocarbon radical such as C$_1$–C$_{20}$-alkyl or C$_6$–C$_{14}$-aryl, in particular methyl.

The radicals R$^1$, R$^2$, R$^3$ and R$^4$ are, independently of one another, identical or different. Preferably, the radicals R$^1$, R$^2$, and R$^3$ and R$^4$ are identical and are each a C$_1$–C$_{20}$-hydrocarbon radical such as C$_1$–C$_{20}$-alkyl or C$_6$–C$_{14}$-aryl, in particular methyl.

Examples of metallocene compounds of the formula II are:
bis(dimethylamido)[η$^5$:η$^5$-2,2-(cyclopentadienyl)(indenyl) propylidene)]-zirconium
bis(dimethylamido)[η$^5$:η$^5$-2,2-(cyclopentadienyl)(indenyl) propylidene)]-hafnium
bis(dimethylamido)[η$^5$:η$^5$-2,2-(fluorenyl)(indenyl) propylidene)]zirconium
bis(dimethylamido)[η$^5$:η$^5$-2,2-(fluorenyl)(indenyl) propylidene)]hafnium
bis(dimethylamido)[η$^5$:η$^5$-2,2-(methylcyclopentadienyl)(indenyl)-propylidene)]zirconium
bis(dimethylamido)[η$^5$:η$^5$-2,2-(fluorenyl)(2-methylindenyl)propylidene)]-zirconium
bis(dimethylamido)[η$^5$:η$^5$-2,2-(tetramethylcyclopentadienyl)(indenyl)-propylidene)]zirconium
bis(dimethylamido)[η$^5$:η$^5$-2,2-(fluorenyl)(2-ethylindenyl) propylidene)]-zirconium
bis(dimethylamido)[η$^5$:η$^5$-2,2-(cyclopentadienyl)(2-methylindenyl)-propylidene)]zirconium
bis(dimethylamido)[η$^5$:η$^5$-2,2-(cyclopentadienyl)(2-ethylindenyl)-propylidene)]zirconium
bis(dimethylamido)[η$^5$:η$^5$-2,2-(cyclopentadienyl)(3-trimethylsilylindenyl)-propylidene)]zirconium
bis(dimethylamido)[η$^5$:η$^5$-2,2-(methylcyclopentadienyl)(2-methylindenyl)-propylidene)]zirconium
bis(dimethylamido)[η$^5$:η$^5$-2,2-(methylcyclopentadienyl)(2-ethylindenyl)-propylidene)]zirconium
bis(dimethylamido)[η$^5$:η$^5$-2,2-(methylcyclopentadienyl)(3-trimethylsilyl-indenyl)propylidene)]zirconium bis(dimethylamido)[η$^5$:η$^5$-2,2-(methylindenyl)(indenyl)-propylidene)]zirconium bis(dimethylamido)[η$^5$:η$^5$-2,2-(bis(indenyl)propylidene)]zirconium The metallocene compound of the formula I or II can be prepared by reacting a compound of the formula III, where L is a π-ligand, L' is a π-ligand, T is a bridge and m is 1 or 2, with a compound of the formula IV, where M is a tetravalent metal and R$^1$, R$^2$, and R$^4$ are, independently of one another, identical or different and are each a hydrogen atom or a $C_1$–$C_{20}$-hydrocarbon radical

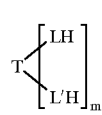   (III)

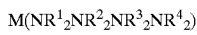   (IV)

The reaction is preferably carried out in an aprotic solvent such as toluene or hexane. The temperature can be between −78 and 140° C., preferably from 0° C. to 110° C. The compound of the formula III can be used in excess; preference is given to using 1 equivalent of the compound of the formula III and 1 equivalent of the metal tetramide of the formula IV.

Methods of preparing compounds of the formula III are known (Chem. Ber. 1990, 123, 1649–1651). Methods of preparing compounds of the formula IV are likewise known (J. Chem. Soc. 1960, 3857–3861).

In the process of the invention, preference is given to using a catalyst which comprises at least one metallocene compound of the formula I and at least one cocatalyst. It is also possible to use mixtures of two or more metallocene compounds, in particular for preparing reactor blends or cycloolefin copolymers having a broad or multimodal molecular weight distribution.

A suitable cocatalyst in the process of the invention is in principle any compound which, owing to its Lewis acidity, can convert the neutral metallocene compound into a cation and stabilize the latter ("labile coordination"). In addition, the cocatalyst or the anion formed therefrom should undergo no further reactions with the cation formed (EP-A-427 697). As cocatalyst, preference is given to using an aluminum compound and/or a boron compound.

The boron compound preferably has the formula $R^a_xNH_{4-x}BR^b_4$, $R^a_xPH_{4-x}BR^b_4$, $R^a_3CBR^b_4$ or $BR^b_3$, where x is from 1 to 4, preferably 3, the radicals $R^a$ are identical or different, preferably identical, and are $C_1$–$C_{10}$-alkyl or $C_6$–$C_{18}$-aryl, or two radicals $R^a$ together with the atoms connecting them form a ring, and the radicals $R^b$ are identical or different, preferably identical, and are $C_6$–$C_{18}$-aryl which may be substituted by alkyl, haloalkyl or fluorine. In particular, $R^a$ is ethyl, propyl, butyl or phenyl and $R^b$ is phenyl, pentafluorophenyl, 3,5-bis(trifluoromethyl)phenyl, mesityl, xylyl or tolyl (EP-A-277 003, EP-A-277 004 and EP-A-426 638).

The cocatalyst used is preferably an aluminum compound such as aluminoxane and/or an aluminum alkyl.

The cocatalyst used is particularly preferably an aluminoxane, in particular of the formula Va for the linear type and/or the formula Vb for the cyclic type,

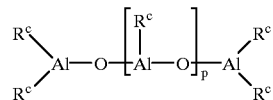   (Va)

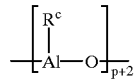   (Vb)

where, in the formulae Va and Vb, the radicals $R^c$ are identical or different and are each hydrogen or a $C_1$–$C_{20}$-hydrocarbon group such as a $C_1$–$C_{18}$-alkyl group, a $C_6$–$C_{18}$-aryl group or benzyl and p is an integer from 2 to 50, preferably from 10 to 35.

The radicals $R^c$ are preferably identical and are hydrogen, methyl, isobutyl, phenyl or benzyl, particularly preferably methyl.

If the radicals $R^c$ are different, then they are preferably methyl and hydrogen or alternatively methyl and isobutyl, with hydrogen or isobutyl preferably being present in a proportion of from 0.01 to 40% by number (of the radicals $R^c$).

The methods of preparing the aluminoxanes are known. The exact spatial structure of the aluminoxanes is not known (J. Am. Chem. Soc. (1993) 115, 4971). For example, it is conceivable that chains and rings can join to form larger two-dimensional or three-dimensional structures.

Regardless of the method of preparation, all aluminoxane solutions have in common a varying content of unreacted aluminum starting compound, which is present in free form or as adduct.

It is possible to preactivate the metallocene compound with a cocatalyst, in particular an aluminoxane, before use in the polymerization reaction. This significantly increases the polymerization activity. The preactivation of the metallocene compound is preferably carried out in solution. The metallocene compound is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene compound can be used in the same concentration, but it is preferably used in an amount of from $10^{-4}$ to 1 mol per mol of aluminoxane. The preactivation time is from 5 minutes to 60 hours, preferably from 5 to 60 minutes. The preactivation is carried out at a temperature of from −78 to 150° C., preferably from 0 to 80° C.

The metallocene compound is preferably employed in a concentration, based on the transition metal, of from $10^{-3}$ to $10^{-8}$ mol, preferably from $10^{-4}$ to $10^{-7}$ mol, of transition metal per dm$^3$ of solvent of per dm$^3$ of reactor volume. The aluminoxane is preferably used in a concentration of from $10^{-6}$ to $10^{-1}$ mol, preferably from $10^{-5}$ to $10^{-2}$ mol, per dm$^3$ of solvent or per dm$^3$ of reactor volume. The other cocatalysts mentioned are used in approximately equimolar amounts to the metallocene compound. However, higher concentrations are also possible in principle.

The aluminoxane can be prepared in various ways by known methods. One of the methods is, for example, reacting an aluminum hydrocarbon compound and/or a hydridoaluminum hydrocarbon compound with water (gaseous, solid, liquid or bound—for example as water of crystallization) in an inert solvent such as toluene. To prepare an aluminoxane having different radicals $R^c$, for example, two or more different trialkylaluminums corresponding to the desired composition are reacted with water (S. Pazynkiewicz, Polyhedron 9 (1990) 429, EP-A 302 424).

To remove catalyst poisons present in the olefin, purification using an aluminum compound, preferably an aluminum alkyl such as trimethylaluminum or triethylaluminum, is advantageous. This purification can be carried out either in the polymerization system itself or the olefin is brought into contact with the aluminum compound and subsequently separated off again before addition to the polymerization system.

In the process of the invention, the metallocene compound is preferably reacted with the cocatalyst outside the polymerization reactor in a separate step using a suitable solvent. Application to a support can be carried out during this step.

If solvent is added to the reaction mixture, this is a customary inert solvent such as an aliphatic or cycloaliphatic hydrocarbon, a petroleum or hydrogenated diesel oil fraction or toluene.

The metallocene compound of the formula I is preferably used in the form of its racemate. The metallocene compound is preferably employed in a concentration, based on the transition metal of from $10^{-3}$ to $10^{-8}$ mol, preferably from $10^{-4}$ to $10^{-7}$ mol, of transition metal per $dm^3$ of reactor volume. The aluminoxane is used in a concentration of from $10^{-4}$ to $10^{-1}$ mol, preferably from $10^{-4}$ to $2*10^{-2}$ mol, per $dm^3$ of reactor volume, based on the aluminum content. However, higher concentrations are also possible in principle.

In the process of the invention, at least one cyclic, preferably polycyclic, olefin is polymerized together with at least one acyclic olefin. Polycyclic olefins preferably have the formulae VI, VII, VIII, IX, X or XI

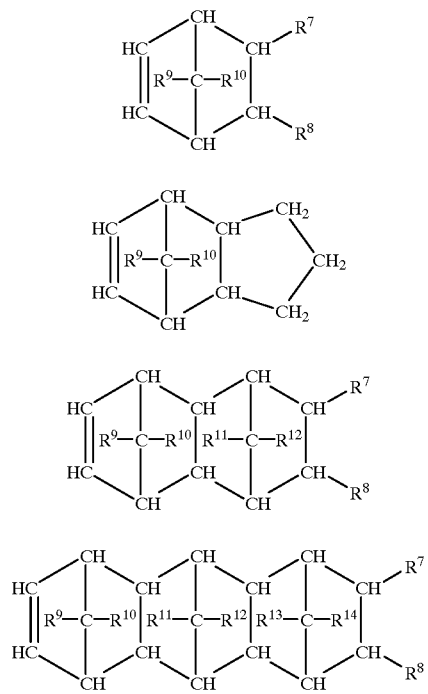

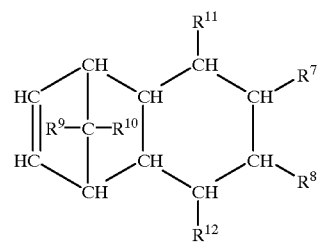

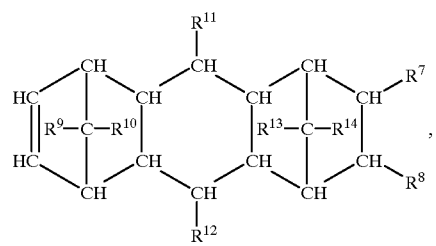

where $R^7$, $R^8$, $R^9$, $R^{10}$, $R^{11}$, $R^{12}$, $R^{13}$ and $R^{14}$ are identical or different and are each a hydrogen atom or a $C_1$–$C_{20}$-hydrocarbon radical such as $C_1$–$C_8$-alkyl or $C_6$–$C_{10}$-aryl, or two or more radicals $R^7$–$R^{14}$ together form a $C_4$–$C_{40}$-ring system, where identical radicals $R^7$–$R^{14}$ in the various formulae can have a different meaning. Particular preference is given to cycloolefins of the formulae VI or VIII, where $R^7$, $R^8$, $R^9$, $R^{10}$, $R^{11}$, $R^{12}$, $R^{13}$ and $R^{14}$ are identical or different and are each a hydrogen atom or a $C_1$–$C_{20}$-hydrocarbon radical, in particular a $C_6$–$C_{10}$-aryl radical or a $C_1$–$C_8$-alkyl radical, where identical radicals $R^7$–$R^{14}$ in the various formulae VI–XI can have a different meaning.

Acyclic olefins are preferably 1-olefins having from 1 to 40, preferably 1–20, carbon atoms. Particular preference is given to 1-olefins of the formula (XII)

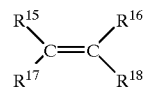

where $R^{15}$, $R^{16}$, $R^{17}$ and $R^{18}$ are identical or different and are each a hydrogen atom or a $C_1$–$C_{20}$-hydrocarbon radical, preferably a $C_6$–$C_{10}$-aryl radical and a $C_1$–$C_8$-alkyl radical. Examples of acyclic olefins are ethylene and propylene.

If desired, one or more monocyclic olefins, in particular of the formula (XIII)

where n is from 2 to 10, are also used in the process of the invention.

In particular, copolymers of polycyclic olefins, preferably of the formulae VI and VIII, with ethylene are prepared.

Particularly preferred polycyclic olefins are norbornene and tetracyclododecene, with these being able to be substituted by ($C_1$–$C_6$)-alkyl. They are preferably copolymerized with ethylene; ethylene-norbornene copolymers are of particular importance.

In the process of the invention, the polycyclic olefin is preferably used in an amount of from 0.1 to 99.9% by weight, the monocyclic olefin in an amount of from 0 to 99.9% by weight and the acyclic olefin in an amount of from 0.1 to 99.9% by weight, in each case based on the total amount of monomers.

The concentration of the acyclic olefin used is given by its solubility in the reaction medium at a given pressure and a given temperature.

For the purposes of the present invention, polycyclic olefins, monocyclic olefins and acyclic olefins also include mixtures of two or more olefins of the respective type. This means that, apart from polycyclic bicopolymers, it is also possible to prepare tercopolymers and multicopolymers by the process of the invention. Copolymers of monocyclic olefins and acyclic olefins can also be obtained by means of the process of the invention.

Among the monocyclic olefins, preference is given to cyclopentene which may be substituted.

The process of the invention is preferably carried out at temperatures of from −78 to 150° C., in particular from 0 to 100° C., and a pressure of from 0.01 to 64 bar.

The polymerization is carried out in the liquid cycloolefin itself or in a cycloolefin solution, with the pressure advantageously being above 1 bar.

In the preparation of copolymers, the molar ratios of the polycyclic olefin to the open-chain olefin used can be varied within a wide range. Preference is given to using molar ratios of from 3:1 to 100:1 of cycloolefin to open-chain olefin. Selection of the polymerization temperature, the concentration of the catalyst component and the molar ratio used or the pressure of the gaseous, open-chain olefin enables the proportion of comonomer incorporated to be controlled almost at will. Preference is given to incorporation of between 20 and 80 mol % of the cyclic components and particular preference is given to incorporation of between 40 and 60 mol % of the cyclic components.

The polymerization can also be carried out in a plurality of stages, with block copolymers also being able to be formed (EP-A-560 090).

The mean molar mass of the polymer formed can also be controlled in a known manner by metering in hydrogen, varying the catalyst concentration or varying the temperature.

The polydispersity $M_w/M_n$ of the cycloolefin copolymers is from 1.9 to 3.5 and the molecular weight distribution is therefore quite narrow. This results in a property profile which makes the cycloolefin copolymers particularly suitable for injection molding.

The process of the invention makes possible the preparation of amorphous cycloolefin copolymers which contain no partially crystalline ethylene polymers. The copolymers are transparent, hard and can be processed thermoplastically. The yield stresses (in accordance with DIN 53457) are in the range from 50 to 100 MPa, preferably between 55 and 70 MPa. Both during extrusion and during injection molding, no decomposition reactions or a drop in viscosity have been found at temperatures of 300° C.

The cycloolefin copolymers prepared according to the invention are particularly suitable for the production of shaped parts such as extruded parts (e.g. films, hoses, tubes, rods and fibers) or injection-molded articles of any shape and size.

The films can be extruded films, calendered films, cast films, monoaxially and biaxially oriented films or multilayer films and are suitable, in particular, as food packaging films or blister packaging. They have a high barrier action against water and a low gas permeability. Cycloolefin copolymers prepared according to the invention are also suitable as an additive in other polymer films (in particular polyolefin films such as polypropylene films or polyethylene films), for example for the purposes of improving flow, improving the ability to apply a surface coating, influencing the modulus of elasticity and for producing opaque films.

An important property of the cycloolefin copolymers prepared according to the invention is their transparency. This makes the optical applications of the extruded or injection-molded parts produced from the cycloolefin copolymers particularly important. The index of refraction, determined using an Abbe refractometer and mixed light, of the reaction products described in the examples below is in the range between 1.520 and 1.555. Since the index of refraction is very close to that of crown glass (n=1.51), the products according to the invention can be used as a substitute for glass in various applications, for example lenses, prisms, support plates and films for optical data storage, for video disks, for compact disks, as covering and focusing disks for solar cells, as covering and scattering disks for power optics, as optical waveguides in the form of fibers and films.

In impact-modified form, the cycloolefin copolymers prepared according to the invention can also be used as a structural material in various industrial fields (EP-A-566 988).

The cycloolefin copolymers obtained according to the invention can also be used for producing polymer alloys. The alloys can be produced in the melt or in solution. The alloys have, in each case, a property combination of the components which is favorable for certain applications. The following polymers are preferably used for alloys with the cycloolefin copolymers of the invention:

polyethylene, polypropylene, ethylene-propylene copolymers, polybutylene, poly(4-methyl-1-pentene), polyisoprene, polyisobutylene, natural rubber, poly(methyl methacrylate), further polymethacrylates, polyacrylates, acrylate-methacrylate copolymers, polystyrene, styrene-acrylonitrile copolymers, bisphenol A polycarbonate, further polycarbonates, aromatic polyester carbonates, polyethylene terephthalate, polybutylene terephthalate, amorphous polyarylates, nylon 6, nylon 66, further polyamides, polyaramides, polyether ketones, polyoxymethylene, polyoxyethylene, polyurethanes, polysulfones, polyether sulfones, polyvinylidene fluoride.

The process of the invention proceeds with high activity and gives, in particular, transparent cycloolefin copolymers which have high tear strengths.

The glass transition temperatures Tg quoted in the following examples were determined by means of DSC (Differential Scanning Calorimetry) at a heating rate of 20° C./min. the viscosity numbers quoted were determined in accordance with DIN 53728. The mechanical properties were measured in a tensile test (DIN 53457, Instron 4302).

The measure used for the catalyst activity was the yield of polymer per unit time and per mmol of metallocene;

$$\text{Activity} = \frac{\text{Polymer (g)}}{\text{Time [h]} \times \text{amount of metallocene [mmol]}} = A^*$$

General procedures: Preparation and handling of organometallic compounds was carried out with exclusion of air and moisture under argon (Schlenk technique). All solvents required were freed of air and moisture before use by boiling for a number of hours over a suitable desiccant and subsequent distillation under argon.

The diketones and ketoaldehydes used as starting compounds were prepared by literature methods. Cyclopentadiene and methylcyclopentadiene were obtained by cracking of the dimers and were stored at −35° C.

The Al/CH$_3$ ratio in the aluminoxane was determined by decomposition of the sample with H$_2$SO$_4$ and determination of the volume of the hydrolysis gases formed under standard conditions and also by complexometric titration of the aluminum in the then dissolved sample using the Schwarzenbach method.

The compounds were characterized using $^1$H-NMR, $^{13}$C-NMR and IR spectroscopy.

The following examples illustrate the invention:

All glass apparatus was baked out in vacuo and flushed with argon. All operations were carried out with exclusion of moisture and oxygen in Schlenk vessels. The solvents used were distilled from a Na/K alloy under argon.

Toluene-soluble methylaluminoxane was used for the examples of polymerization as a 10% strength by weight toluene solution having a mean degree of oligomerization of n=20 (Witco). The aluminum content determined was 36 mg of Al/ml.

EXAMPLE 1

Bis(dimethylamido)[η$^5$:η$^5$-2,2-(cyclopentadienyl)(indenyl)propylidene]-zirconium A solution of zirconium amide (416 mg, 1.55 mmol) in 25 ml of toluene is cooled to −78° C. and subsequently a solution of 345 mg of the ligand in 10 ml of toluene is added dropwise. The solution is warmed to room temperature and after stirring for 12 hours is heated at 80° C. for 3 hours. The solvent is removed under reduced pressure and the complex is obtained in the form of a yellow-orange solid in a yield of 99% (613 mg).

$^1$H-NMR (400 MHz, C$_6$D$_6$):δ[ppm]=1.57, 1.89 (s, 6H, C(CH$_3$)$_2$), 2.46, 2.81 (s, 12H, N(CH$_3$)$_2$), 5.29 (m, 1H, CH in C$_5$H$_4$), 5.80 (m, 2H, CH in C$_5$H$_4$ and C$_9$H$_7$), 5.99 (m, 1H, CH in C$_5$H$_4$), 6.08 (m, 1H, CH in C$_5$H$_4$), 6.59 (d, 1H, $^3$J(H,H)=3.0 Hz, CH in C$_9$H$_7$), 6.69 (m, 1H, CH in C$_9$H$_7$), 7.49 (m, 1H, CH in C$_9$H$_7$), 7.62 (m, 1H, CH in C$_9$H$_7$).

MS(CI): m/e (%)=708 (10)[2M$^+$−2NMe$_2$], 398 (100) [M$^+$], 355 (45) [M$^{30}$−NMe$_2$], 311 (21%)[M$^+$−2 NMe$_2$].

EXAMPLE 2

Bis(dimethylamido)[η$^5$:η$^5$-2,2-(cyclopentadienyl)(indenyl)propylidene]-hafnium A solution of hafnium amide (833 mg, 1.55 mmol) in 25 ml of xylene is cooled to—78° C. and subsequently a solution of 522 mg of the ligand in 10 ml of xylene is added dropwise. The solution is warmed to room temperature and after stirring for 2 hours is heated at 150° C. for 8 hours. The solvent is removed under reduced pressure and the complex is recrystallized from a little pentane. The complex precipitates in the form of a yellow-orange solid (95% yield, 613 mg).

$^1$H-NMR (400 MHz, C$_6$D$_6$):δ[ppm]=1.57, 1.88 (s, 6H, C(CH$_3$)$_2$), 2.51, 2.85 (s, 12H, N(CH$_3$)$_2$), 5.29 (m, 1H, CH in C$_5$H$_4$), 5.70–5.80 (m, 2H, CH in C$_5$H$_4$ and C$_9$H$_7$), 6.00 (m, 1H, CH in C$_5$H$_4$), 6.04 (m, 1H, CH in C$_5$H$_4$), 6.53 (d, 1H, $^3$J(H,H)=3.0 Hz, CH in C$_9$H$_7$), 6.71 (m, 1H, CH in C$_9$H$_7$), 6.87 (m, 1H, CH in C$_9$H$_7$), 7.49 (m, 1H, CH in C$_9$H$_7$), 7.63 (m, 1H, CH in C$_9$H$_7$).

MS(CI): m/e (%)=620 (100), 600 (18), 512 (24), 497 (28), 442 (17), 399 (25), 222 (26), 207 (26), 115 (8), 107 (20).

Polymerization Examples

Example A:

A 1.5 dm$^3$ autoclave which has been thoroughly flushed beforehand with ethene is charged with 600 cm$^3$ of an 85% strength by weight solution of norbornene in toluene. The solution was saturated with ethene by repeated pressurization with ethene (6 bar). 5 cm$^3$ of methylaluminoxane solution in toluene (10.1% strength by weight solution of methylaluminoxane having a molar mass of 1300 g/mol determined by cryoscopy) were metered in countercurrent into the reactor thus prepared and the mixture was stirred for 30 minutes at 70° C. A solution of 1.5 mg of bis(dimethylamido)[η$^5$:η$^5$-2,2-(cyclopentadienyl)indenyl)-propylidene]zirconium (I) in 5 cm$^3$ of a solution of methylaluminoxane in toluene was added after a preactivation time of 15 minutes. (If hydrogen regulation is to be used, hydrogen can be injected at this point).

Polymerization was carried out for one hour at 70° C. while stirring (750 rpm), with the ethene pressure being maintained at 6 bar by metering in further amounts.

At the end of the reaction time, the polymerization mixture was drained into a vessel and immediately introduced into 5 dm$^3$ of acetone, stirred for 10 minutes and the precipitated product was subsequently filtered off. The filter cake was washed alternatively with three portions of 10% strength hydrochloric acid and three portions of acetone. Finally, it was washed with water until neutral, the residue was slurried in acetone and filtered again. The polymer thus purified was dried for 15 hours at 80° C. under reduced pressure (0.2 bar).

Drying gave 44 g of colorless polymer which had a glass transition temperature of 193° C., a viscosity number of 69 cm$^3$/g, a yield stress of 64 MPa and an elongation at break of 3.3%. The activity A was 10842 g of polymer/h x mmol.

Example B:

Example A was repeated at an ethylene pressure of 18 bar and a polymerization temperature of 90° C. The yield of purified and dried polymer was 152 g. The polymer had a glass transition temperature of 150° C., a viscosity number of 70 cm$^3$/g, a yield stress of 62 MPa and an elongation at break of 3.5%. The activity A° was 56182 g of polymer/h x mmol.

Example C:

The procedure of Example B was repeated, but the metallocene used was 0.5 mg of isopropylidenebis(1-indenyl)bis(N,N-dimethylamido)zirconium (II). This gave 114 g of purified and dried polymer having a glass transition temperature of 143° C., a viscosity number of 152 cm$^3$/g.

Example D:

The procedure of Example A was repeated, but the metallocene used was 0.1 mg of dimethylsilanediyl(9-(2,7-di-tert-butyl)fluorenyl)cyclopentadienyl-bis(N,N-dimethylamido)zirconium (III). This gave 17 g of purified and dried polymer having a glass transition temperature of 143° C. and a viscosity number of 267 cm$^3$/g.

Example E:

The procedure of Example A was repeated, but the metallocene used was 0.2 mg of isopropylidene(9-fluorenyl)cyclopentadienyl-bis(N,N-dimethylamido)zirconium (IV).

This gave 64 g of purified and dried polymer having a glass transition temperature of 151° C. and a viscosity number of 147 cm³/g.

TABLE

Polymerization results

| Example No. | Metallocene | Temp. (° C.) | Ethylene pressure (bar) | Amount of metallocene (mg) | Yield (g) | VN (cm3/g) | Tg (° C.) | Method (toluene) |
|---|---|---|---|---|---|---|---|---|
| A | I | 70 | 6 | 1.5 | 44 | 69 | 193 | 85% strength solution |
| B | I | 90 | 18 | 1 | 152 | 70 | 150 | 85% strength solution |
| C | II | 90 | 18 | 0.5 | 114 | 152 | 143 | 85% strength solution |
| D | III | 70 | 6 | 0.1 | 17 | 267 | 143 | 85% strength solution |
| E | IV | 70 | 6 | 0.2 | 64 | 147 | 151 | 85% strength solution |

We claim:

1. A process for preparing a cycloolefin copolymer, comprising:

co-polymerizing at least one cyclic olefin and at least one acyclic olefin in the presence of a catalyst comprising at least one metallocene compound of the formula I

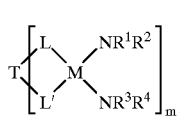

(I)

where m is 1 or 2; L is a monocyclic, fused bicyclic, or fused tricyclic π-ligand, L' is a monocyclic, fused bicyclic, or fused tricyclic π-ligand, and, when m is 1, L and L' are different from each other, at least one of L and L' being monocyclic when the other is fused bi- or fused tricyclic, and at least one of L and L' being fused bicyclic when the other is monocyclic or fused tricyclic; T is a bridge between L and L'; M is a tetravalent transition metal; and $R^1$, $R^2$, $R^3$ and $R^4$ are, independently of one another, identical or different and are each a hydrogen atom or a $C_1$-$C_{20}$-hydrocarbon radical.

2. The process as claimed in claim 1, wherein the catalyst further comprises at least one cocatalyst.

3. The process as claimed in claim 1, wherein L and L' are substituted or unsubstituted cyclopentadienyl, substituted or unsubstituted indenyl, or substituted or unsubstituted fluorenyl.

4. The process as claimed in claim 1, wherein m is 2.

5. The process as claimed in claim 1, wherein M of the formula I is titanium, zirconium, hafnium, vanadium, niobium, tantalum, scandium, yttrium or a rare earth metal, L is a substituted or unsubstituted cyclopentadienyl group, L' is a substituted or unsubstituted cyclopentadienyl group which is identical to or different from L; and, when m is 1, T is 1 to 4 bridging units of the formula ($R^5R^6X$), where the X radicals of each of the bridging units are, independently of one another, identical or different and are carbon, silicon, germanium or tin, the radicals $R^5$ and $R^6$ are, independently of one another, identical or different and are each a hydrogen atom or a $C_1$-$C_{30}$-hydrocarbon radical;

and, when m is 2, T is carbon, silicon, germanium, or tin.

6. The process as claimed in claim 5, wherein M is titanium, zirconium, or hafnium; $R^5$ and $R^6$ are identical or different and are $C_1$-$C_{20}$-alkyl or $C_6$-$C_{20}$-aryl, and $R^1$, $R^2$, $R^3$, and $R^4$ are identical or different and are $C_1$-$C_{20}$-alkyl or $C_6$-$C_{14}$-aryl.

7. The process as claimed in claim 1, wherein a metallocene compound of the formula I has been converted into a cationic or labile coordination form of said metallocene compound with a cocatalyst having Lewis acidity.

8. The process as claimed in claim 7, wherein said cocatalyst is an aluminum compound, a boron compound, or a combination thereof.

9. The process as claimed in claim 7, wherein the resulting cycloolefin copolymer is resistant to decomposition at a temperature of 300° C. and has the following properties:

yield stress, as measured by DIN 53457, of 50 to 100 MPa, and a refractive index ranging from 1.520 to 1.555.

10. A method of using a metallocene compound of the formula I

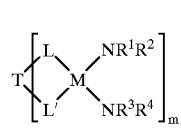

(I)

where:

m is 1 or 2,

L is a mono-cyclic fused bi-cyclic or tri-cyclic π-ligand

L' is a mon-cyclic fused bi-cyclic or fused tri-cyclic π-ligand, and, when m is 1, L and L' are different from each other, at least one of L and L' being monocyclic when the other is fused bi-cyclic or fused tri-cyclic, and at least one of L and L' being fused bicyclic when the other is mono- or fused tri-cyclic, T is a bridge between L and L', M is a tetravalent transition metal, m is 1 or 2, and $R^1$, $R^2$, $R^3$ and $R^4$ are, independently of one another, identical or different and are each a hydrogen atom or a $C_1$-$C_{20}$-hydrocarbon radical, comprising:

co-polymerizing a co-polymerizable monomeric composition containing at least one cyclic olefin in the presence of said metallocene compound or a cation or labile coordination form thereof.

* * * * *